US00PP25664P3

(12) United States Plant Patent

Lintott et al.

(10) Patent No.: US PP25,664 P3

(45) Date of Patent: Jun. 30, 2015

(54) *LEUCANTHEMUM* PLANT NAMED 'REAL DREAM'

(50) Latin Name: *Leucanthemum×superbum*
Varietal Denomination: Real Dream

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 141 days.

(21) Appl. No.: 13/986,665

(22) Filed: May 22, 2013

(65) Prior Publication Data

US 2014/0352014 P1 Nov. 27, 2014

(51) Int. Cl.
*A01H 5/02* (2006.01)

(52) U.S. Cl.
USPC ..... Plt./285

(58) Field of Classification Search
USPC ..... Plt./285
CPC ..... A01H 5/00; A01H 5/0255
See application file for complete search history.

(56) References Cited

PUBLICATIONS

American Nurseryman Perennials for 2013 Dec. 2012, pp. P10-P11.*

* cited by examiner

*Primary Examiner* — June Hwu
(74) *Attorney, Agent, or Firm* — Barbara Campbell; Bethany R. Roahrig; Cochran Freund & Young LLC

(57) ABSTRACT

A new cultivar of *Leucanthemum* plant named 'Real Dream' that is distinguishable by tight clumping habit, mid-dark green foliage and inflorescences comprised of many cream-yellow ray florets arranged in three layers surrounding a yellow central disc and carried on strong stems.

2 Drawing Sheets

Genus and species: *Leucanthemum×superbum.*
Variety denomination: 'Real Dream'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum×superbum* and will be referred to hereinafter by the cultivar name 'Real Dream'. This application is co-pending with the application for the inventor's variety of *Leucanthemum* plant named 'Real Glory' (U.S. Plant patent application Ser. No. 13/986,637).

*Leucanthemum* is a genus within the family Asteraceae in which the commonly referred to "flower" is botanically the inflorescence which is comprised of outer showy ray florets surrounding smaller disc florets.

'Real Dream' arose and was selected from an ongoing breeding program which is conducted by the inventors at the inventors' nursery in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in the fall, and new seedlings are raised and evaluated in the following summer.

'Real Dream' is a seedling selection that resulted from the controlled pollination of a single plant of *Leucanthemum* code number 'L637' (unnamed and unreleased seedling retained from a previous breeding generation) as female parent, using pollen from a single plant of *Leucanthemum* 'Sonnenschein' (unpatented) as male parent. The inventors selected 'Real Dream' based on the criteria of vigor, formal flowers with many petals and strong stems.

'Real Dream' was first asexually propagated by the inventors in West Sussex, United Kingdom in 2008 using the method of vegetative division and subsequently by basal shoot cuttings. Since that time under careful observation 'Real Dream' has been determined uniform, stable and true to type in subsequent generations of asexual propagation.

SUMMARY OF THE INVENTION

The following traits have been repeatedly observed and represent the distinguishing characteristics of 'Real Dream'. In combination these traits set 'Real Dream' apart from all other existing varieties of *Leucanthemum* known to the inventor. 'Real Dream' has not been tested under all possible conditions and phenotypic differences may be observed with variations in environmental, climatic, and cultural conditions, however, without any variance in genotype.

1. 'Real Dream' exhibits tight clumping habit.
2. The foliage of 'Real Dream' is mid-dark green in color.
3. The inflorescence of 'Real Dream' is 8.0 cm in diameter and comprised of ray florets arranged around the central disc.
4. The ray florets of 'Real Dream' are cream-yellow in color.
5. The inflorescence of 'Real Dream' is carried on a strong stiff stem.
6. Flowering of 'Real Dream' commences in early summer and continues until fall.

7. After one year of growth in a 1 gallon container, a plant of 'Real Dream' is 40.0 cm in height and 35.0 cm in width.
8. 'Real Dream' prefers a rich moist well-drained medium.
9. 'Real Dream' is hardy in USDA Zone 5 (−20° F. or −28° C.).

COMPARISON WITH PARENTAL LINES AND KNOWN VARIETY

'Real Dream' is distinguishable from the female parent by the color of its ray florets. Whereas 'L637' exhibits white ray florets, the ray florets of 'Real Dream' are cream-yellow in color. 'Real Dream' is distinguishable from the male parent by plant habit and by color and arrangement of petals. 'Sonnenschein' is a taller variety of *Leucanthemum* and exhibits light cream-white flowers with petals arranged mostly in a single layer. 'Real Dream' is a compact variety with cream-yellow flowers and petals arranged in mostly three layers.

The variety of *Leucanthemum* which the inventor considers to be closest in overall appearance to 'Real Dream' is cream-yellow flowered *Leucanthemum* 'Leumayel' (U.S. Plant Pat. No. 19,242). Whereas the flowers of 'Real Dream' are comprised of three layers of petals, the petals of 'Leumayel' are arranged in a single layer. In addition, the inventors have observed that 'Real Dream' exhibits a higher bud count than 'Leumayel' when both varieties are grown under similar conditions.

BRIEF DESCRIPTION OF THE DRAWINGS

The accompanying color drawings illustrate the overall appearance of the new *Leucanthemum* cultivar named 'Real Dream' showing the color of foliage and flower as true as is reasonably possible to obtain in color reproductions of this type. Color in the drawings may differ from color values cited in the detailed botanical description, which accurately describe the actual color of 'Real Dream'.

The drawing labeled

The drawing labeled

Figure 1:
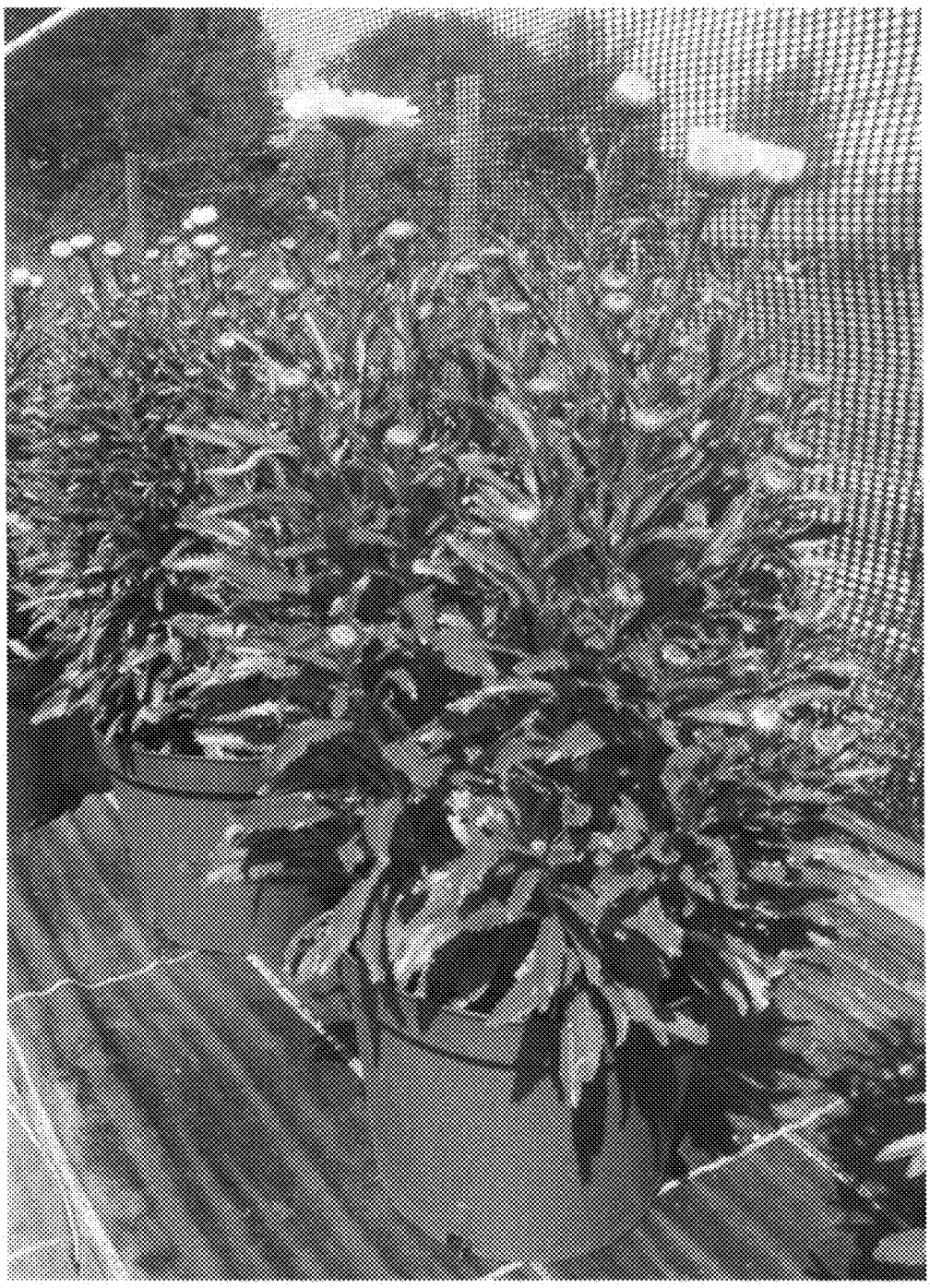
FIG. 1 illustrates two eighteen-month-old plants (from initial cuttings) which have been grown out of doors at the inventor's nursery in West Sussex, United Kingdom. The illustrated plants have not been pinched or treated with any chemical growth regulators.
Figure 2:
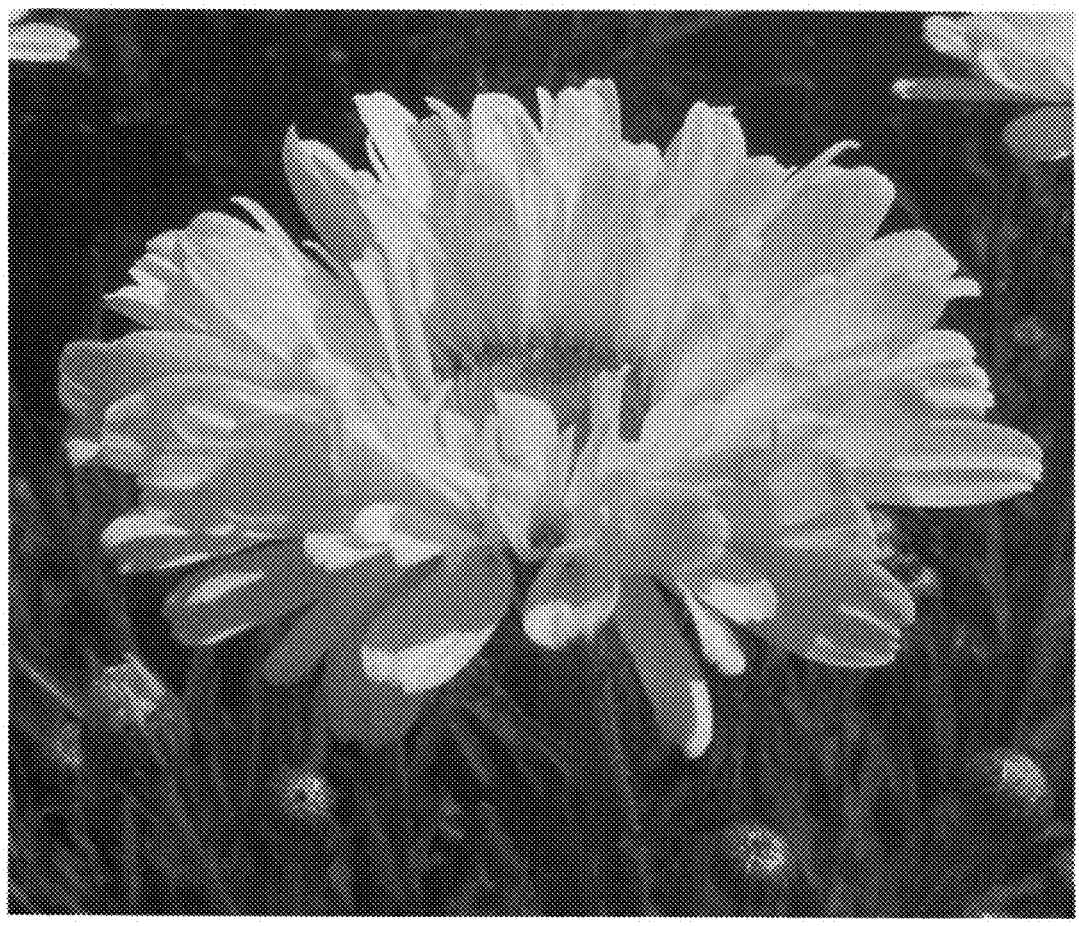
FIG. 2 depicts a close-up view of the inflorescence when freshly open on an eighteen-months-old plant of 'Real Dream'.

Both drawings were made using conventional techniques and although flower and foliage color may appear different from actual color due to light reflectance, it is as accurate as possible by conventional photography.

BOTANICAL DESCRIPTION OF THE PLANT

The following is a detailed botanical description of the new cultivar 'Real Dream'. Observations, measurements, values and comparisons were collected in Santa Barbara, Calif. during summer, from a 12-month-old plant growing out-of-doors in the garden border. Color determinations are made in accordance with The 2007 Royal Horticultural Society Colour Chart from London, England, except where general color terms of ordinary dictionary significance are used.

Botanical classification:

*Family.*—Asteraceae (formerly Compositae).
*Genus.*—*Leucanthemum.*
*Species.*—×*superbum.*
*Denomination.*—'Real Dream'.
*Common name.*—Shasta daisy.
*Habit.*—Tight clumping habit.
*Commercial category.*—Perennial herb.
*Use.*—For garden and landscape.
*Suggested commercial container size.*—4-inch and 1-liter containers.
*Parentage.*—*Leucanthemum*×*superbum* 'Real Dream' is a seedling selection resulting from the deliberate controlled cross-pollination of the following parents: Male parent: *Leucanthemum* 'Sonnenschein' (unpatented). Female parent: *Leucanthemum* code number 'L637' (unnamed and unreleased seedling retained from a previous breeding generation).
*Propagation method.*—Basal shoot cuttings and division.
*Rooting system.*—Fine and fibrous.
*Vigor.*—Vigorous.
*Time to develop roots* (*range*).—14 to 20 days are needed for an initial cutting to develop roots.
*Temperature to develop roots* (*range*).—The recommended air temperature is 20° C. to 21° C.
*Crop time* (*range*).—4 to 6 months to produce a 1-liter container from a basal shoot cutting.
*Plant dimensions* (*one year*).—40.0 cm in height and 35.0 cm in width.
*Cultural requirements.*—Grow in full sun and rich, moist moderately fertile well-draining soil.
*Pest or disease resistance.*—No disease or pest resistance known to the inventor.
*Hardiness.*—USDA Zone 5.

Stem:

*Branching.*—Basal.
*Color.*—RHS 145A.
*Basal stem length.*—15.0 cm.
*Diameter.*—1.0 cm.
*Shape.*—Cylindrical.
*Surface.*—Smooth, glabrous.

Foliage:

*Type.*—Evergreen.
*Arrangement* (*combination*).—Opposite and basal.
*Internode length* (*range*).—0.5 cm to 1.0 cm.
*Division.*—Simple.
*Margin.*—Serrate; teeth spaced at 4.0 mm to 6.0 mm intervals, depth 2.0 mm.
*Apex.*—Acute.
*Base.*—Attenuate.
*Leaf attachment* (*range*).—Basal to sessile.
*Leaf color* (*abaxial surface*).—RHS N137B.
*Leaf color* (*adaxial surface*).—RHS 137D.
*Leaf shape.*—Lanceolate.
*Leaf dimensions* (*when fully expanded*).—21.0 cm in length, 3.3 cm in width.
*Leaf venation.*—Pinnate.
*Vein color* (*both surfaces*).—RHS 145A.
*Leaf surface* (*both surfaces*).—Glabrous.

Inflorescence:

*Inflorescence type.*—Capitulum.
*Inflorescence quantity* (*average*).—30 (including buds) per 2-liter container plant.
*Inflorescence diameter.*—8.0 cm.
*Inflorescence depth.*—4.0 cm.
*Inflorescence shape.*—Radiate. Ray florets densely arranged around receptacle, mostly in three layers.
*Inflorescence color.*—Central disc color: RHS 14A. Ray floret color: RHS 4B fading to RHS 10D.

*Fragrance.*—Musty, characteristic of wild oxeye daisy.
*Aspect.*—Disc facing upward.

Bud:
*Bud dimensions.*—0.50 cm in height and 1.0 cm in diameter.
*Bud shape.*—Flattened sphere.
*Bud color.*—RHS 147B.
*Bud surface.*—Glabrous.
*Blooming season.*—Early summer to fall.

Peduncle:
*Peduncle shape.*—Cylindrical.
*Peduncle length.*—16.0 cm to 30.0 cm.
*Peduncle diameter.*—4.0 mm to 5.0 mm.
*Peduncle surface.*—Furrowed with sparse hairs.
*Peduncle color.*—RHS 144A.
*Peduncle strength.*—Stiff, strong.

Ray florets:
*Ray floret shape.*—Initially cymbiform, becoming flat when fully expanded.
*Ray floret quantity.*—50 to 60 per inflorescence.
*Ray floret arrangement.*—Radiate.
*Ray floret corolla tube dimensions.*—7.0 mm in length, 1.5 mm in diameter.
*Ray floret corolla tube color.*—RHS 144C.

Petals:
*Petal shape.*—Elliptic, lightly ribbed.
*Petal surface* (*abaxial*).—Glabrous.
*Petal surface* (*adaxial*).—Pubescent.
*Petal apex.*—Rounded, emarginate.
*Petal margin.*—Entire.
*Petal dimensions.*—3.0 cm in length and 1.0 cm in width.
*Petal color* (*when is first fully open*).—RHS 4B except apex RHS 7C.
*Petal color* (*at* 10 *days from first fully open*).—RHS 10D except apex RHS 10A.

Involucral bract:
*Quantity* (*average*).—Greater than 40 per inflorescence, overlapping.
*Bract color* (*abaxial and adaxial surfaces*).—RHS 147B.
*Bract length.*—9.0 mm.
*Bract width.*—3.0 mm.
*Bract apex.*—Rounded.
*Bract base* (*range*).—Rounded to truncate.
*Bract surface* (*both surfaces*).—Glabrous.
*Bract shape.*—Lanceolate.
*Bract margin.*—Ciliate, fine hairs, color RHS 175A.

Disc floret:
*Disc diameter.*—3.0 cm.
*Disc floret quantity.*—Numerous, approximately 400 to 500 per inflorescence, massed at center of receptacle.
*Disc floret color.*—RHS 14A.
*Disc floret dimensions.*—4.0 mm in depth and 1.0 mm in diameter.
*Disc floret shape.*—Tubular, rarely opens.
*Disc floret petals.*—Ranges from 3 to 5 in number, basally fused.
*Disc floret petal color.*—RHS 14A.
*Disc floret petal apex.*—Acute.
*Receptacle color.*—RHS 147B.
*Receptacle shape.*—Convex.
*Receptacle dimensions.*—0.5 cm in height and 2.5 cm in diameter.
*Lastingness of inflorescence* (*range*).—10 to 12 days on the plant. Ray florets persistent.

Reproductive organs:
*Ray flowers.*—Androecium (stamens, anthers, filaments, and pollen): Absent. Pistil: 1.5 mm in length. Stigma: 1.0 mm in length, appears bifid, color is light brown. Ovary: Superior, globose, less than 1.0 mm in diameter and color is RHS 144D.
*Disc flowers.*—General: Stigma, style, and ovary not observed. Stamens: 5, probably fused appearing as 1; length is 1.0 mm and color is RHS 175A. Pollen: Low amount; color is close to RHS 15A (Yellow-Orange). Pistil: 1, less than 1.0 mm in length.

Seed: None observed to date.

We claim:

1. A new and distinct cultivar of *Leucanthemum* plant named 'Real Dream' as described and illustrated herein.

* * * * *